(12) United States Patent
Desai et al.

(10) Patent No.: US 7,191,007 B2
(45) Date of Patent: Mar. 13, 2007

(54) SPATIALLY DECOUPLED TWIN SECONDARY COILS FOR OPTIMIZING TRANSCUTANEOUS ENERGY TRANSFER (TET) POWER TRANSFER CHARACTERISTICS

(75) Inventors: Resha H. Desai, Poland, OH (US); William L. Hassler, Jr., Cincinnati, OH (US)

(73) Assignee: Ethicon Endo-Surgery, Inc, Cincinnati, OH (US)

( * ) Notice: Subject to any disclaimer, the term of this patent is extended or adjusted under 35 U.S.C. 154(b) by 265 days.

(21) Appl. No.: 10/876,057

(22) Filed: Jun. 24, 2004

(65) Prior Publication Data
US 2006/0020305 A1   Jan. 26, 2006

(51) Int. Cl.
*A61N 1/08* (2006.01)
(52) U.S. Cl. .......................... 607/33; 607/61
(58) Field of Classification Search ............ 607/32, 607/33, 60, 61
See application file for complete search history.

(56) References Cited

U.S. PATENT DOCUMENTS

| | | | |
|---|---|---|---|
| 4,581,018 A | 4/1986 | Jassawalla et al. | |
| 5,507,737 A | 4/1996 | Palmskog | |
| 5,715,837 A | 2/1998 | Chen | |
| 5,733,313 A | 3/1998 | Barreras, Sr. et al. | |
| 5,974,873 A | 11/1999 | Nelson | |
| 5,991,665 A * | 11/1999 | Wang et al. | 607/61 |
| 6,009,350 A | 12/1999 | Renken | |
| 6,058,330 A * | 5/2000 | Borza | 607/61 |
| 6,102,678 A | 8/2000 | Peclat | |
| 6,115,634 A | 9/2000 | Donders et al. | |
| 6,315,769 B1 | 11/2001 | Peer et al. | |
| 6,327,504 B1 | 12/2001 | Dolgin et al. | |
| 6,366,817 B1 | 4/2002 | Kung | |
| 6,430,444 B1 | 8/2002 | Borza | |
| 6,463,329 B1 | 10/2002 | Goedeke | |
| 6,482,177 B1 | 11/2002 | Leinders | |
| 6,505,077 B1 | 1/2003 | Kast et al. | |
| 6,542,350 B1 | 4/2003 | Rogers | |
| 2003/0171792 A1 * | 9/2003 | Zarinetchi et al. | 607/61 |

FOREIGN PATENT DOCUMENTS

WO    WO 00 72899    12/2000

OTHER PUBLICATIONS

EPO Search Report, Application No. 05253918.6, Nov. 16, 2005, pp. 1-3.

* cited by examiner

*Primary Examiner*—Robert E. Pezzuto
*Assistant Examiner*—Tammie K. Heller

(57) ABSTRACT

An implantable device, such as an infuser device for bidirectional hydraulically controlling a medical artificial sphincter, enhances power transfer characteristics to a secondary coil thereby allowing implantation to greater physical depths and/or enclosing the secondary coil within a housing of the infuser device. The enhanced power transfer is achieved with multiple coils that are longitudinally aligned and physical and electrical parallel to form the secondary loop of a transcutaneous energy transfer system (TET) instead of a single coil. It better optimizes the power transfer from a parallel tuned tank circuit primary coil to an implanted secondary series tuned tank circuit coil.

23 Claims, 13 Drawing Sheets

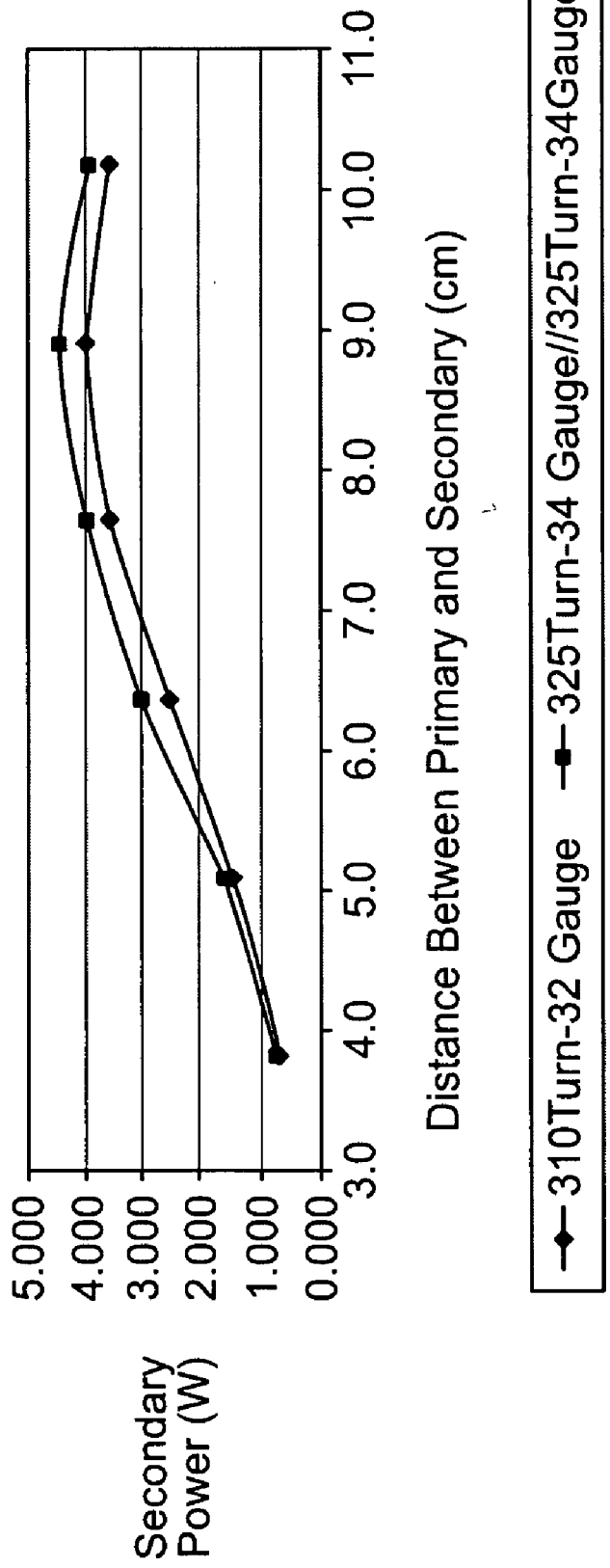

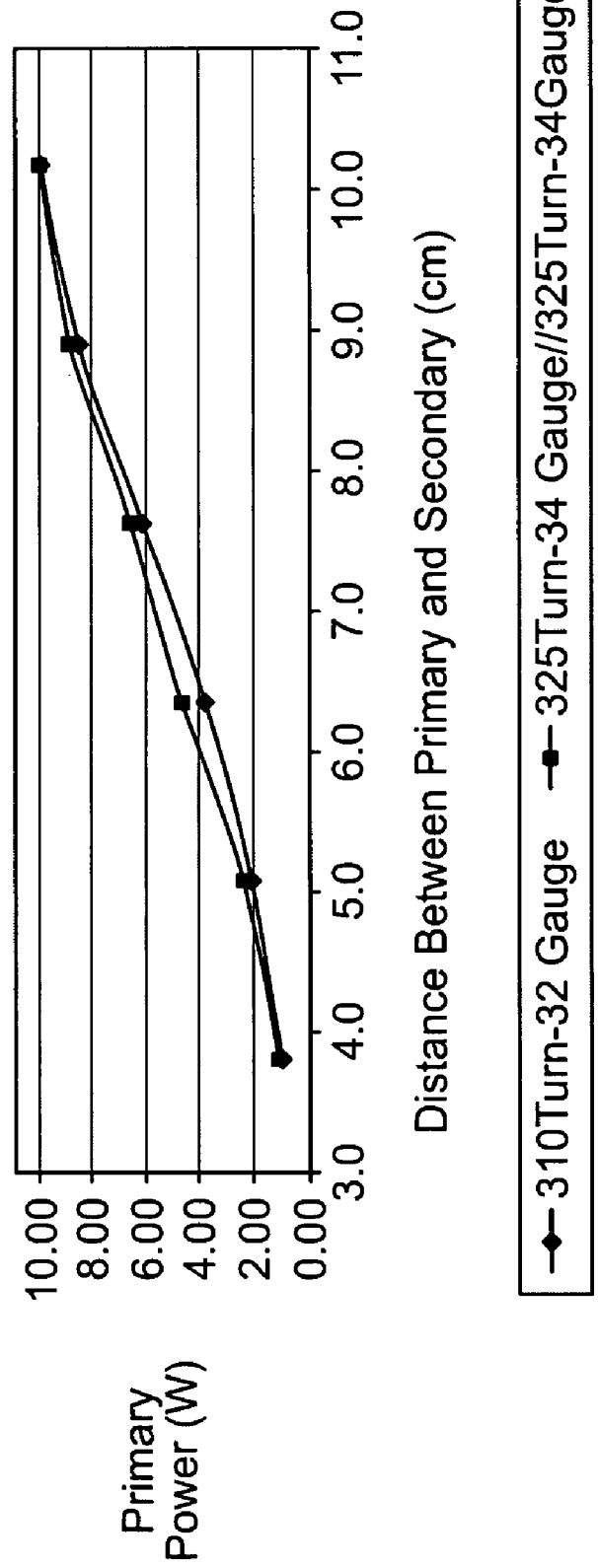

325Turns-34Gauge//325Turns-34Gauge (series tuned)

310Turns-32Gauge (series tuned)

SPATIALLY DECOUPLED TWIN SECONDARY COILS FOR OPTIMIZING TRANSCUTANEOUS ENERGY TRANSFER (TET) POWER TRANSFER CHARACTERISTICS

CROSS REFERENCE TO RELATED APPLICATIONS

The present application is related to four co-pending and commonly-owned applications filed on even date herewith, the disclosure of each being hereby incorporated by reference in their entirety, entitled respectively:

"TRANSCUTANEOUS ENERGY TRANSFER PRIMARY COIL WITH A HIGH ASPECT FERRITE CORE" to J. Giordano, Daniel F. Dlugos, Jr. & William L. Hassler, Jr., Ser. No. 10/876,313;

"MEDICAL IMPLANT HAVING CLOSED LOOP TRANSCUTANEOUS ENERGY TRANSFER (TET) POWER TRANSFER REGULATION CIRCUITRY" to William L. Hassler, Jr., Gordon E. Bloom, Ser. No. 10/876,038;

"LOW FREQUENCY TRANSCUTANEOUS TELEMETRY TO IMPLANTED MEDICAL DEVICE" to William L. Hassler, Jr., Ser. No. 10/867,058; and "LOW FREQUENCY TRANSCUTANEOUS ENERGY TRANSFER TO IMPLANTED MEDICAL DEVICE" to William L. Hassler, Jr., Daniel F. Dlugos, Jr. Ser. No. 10/876,307.

FIELD OF THE INVENTION

The present invention pertains to a transcutaneous energy transfer (TET) system, in particular, to a TET system used between an external control module and a deeply implanted medical implant.

BACKGROUND OF THE INVENTION

It is known to surgically implant a medical device in a patient's body to achieve a number of beneficial results. In order to operate properly within the patient, a reliable, consistent power link between the medical implant and an external control module is often necessary to monitor the implant's performance or certain patient parameters and/or to command certain operations by the implant. This power link has traditionally been achieved with TET systems that communicate across a small amount of tissue, such as relatively thin dermal tissue across the front of the patient's shoulder, such as for cardiac pacemakers.

In some instances, multiple coils have been suggested in regard to a TET or telemetry system in order to provide additional flexibility in aligning primary and secondary coils. For instance, U.S. Pat. No. 6,058,330 Borza discloses a transcutaneous system in which multiple coils were used in the secondary circuitry and perhaps also in the primary circuitry. However, in this instance secondary coils are spaced about the patient's body for the purpose of mitigating tissue damage due to long term exposure to strong electromagnetic fields in a continuous application wherein the medical implant is continuously TET powered or continuously engaged in telemetry. Thus, the '330 Borza patent teaches combining the power received from multiple secondary coils that are widely spaced, either a selected one of the secondary coils is receiving a strong electromagnetic signal or multiple secondary coils are simultaneously receiving weaker electromagnetic signals so that the dermal tissue overlying any one secondary coil is not continuously exposed to a strong electromagnetic signal.

Another problem with continuously coupling electromagnetic power to a secondary coil is the inconvenience to the patient of having the primary coil externally fixed in place, hampering movement and causing discomfort. U.S. Pat. No. 6,366,817 to Kung discloses using multiple coils in the primary spaced about the patient with circuitry that detects which primary coil is best oriented to efficiently couple electromagnetic energy to the implanted secondary coil and thus switching current to the selected primary coil.

U.S. Pat. No. 6,463,329 to Goedeke discloses multiple primary telemetry coils whose major surface, defined by their exterior, are parallel to one another and spaced apart. These coils are used to initiate telemetric communication between the programmer or monitor and the implanted device. At the frequencies disclosed, these coils are employed as loop antennas rather than inductively coupled coils. Since the antenna pattern of a loop antenna includes a "null" when very close to the loop, this approach is used to switch between primary coils when necessary to communicate with the secondary coil, thus primarily addressing problems with medical implants placed under a thin layer of dermal tissue that could coincide with the null of a primary coil placed in contact with the patient.

U.S. Pat. No. 5,741,316 to Chen et al. discloses a transmitter coil that has half of the windings on one leg of a horseshoe magnetic conductor in series with another half of the windings on the other leg. The magnetic flux contribution of each winding portion is thereby combined. However, the corresponding requirement for a horseshoe-shaped magnetic core in the implanted device is undesirable due to the increased size. Thus, laterally offset, electrically serial windings would not be a benefit for a secondary coil integral to an implanted device that lacks a horseshoe shaped magnetic conductor.

While these approaches to improving the effectiveness of electromagnetic coupling to a medical implant have merit, we have recognized an application that does not benefit from spaced apart multiple primary coils and/or spaced apart secondary coils, yet a need exists for enhanced power transfer efficiency. An implantable medical device that may benefit from use of enhanced TET is an artificial sphincter, in particular an adjustable gastric band that contains a hollow elastomeric balloon with fixed end points encircling a patient's stomach just inferior to the esophago-gastric junction. These balloons can expand and contract through the introduction of saline solution into the balloon. In generally known adjustable gastric bands, this saline solution must be injected into a subcutaneous port with a syringe needle to reach the port located below the skin surface. The port communicates hydraulically with the band via a catheter. While effective, it is desirable to avoid having to adjust the fluid volume with a syringe needle since an increased risk of infection may result, as well as inconvenience and discomfort to the patient.

To that end, we have recently developed implanted infuser devices that regulate the flow of saline without requiring injection into the subcutaneous port. This system transfers AC magnetic flux energy from an external primary coil to a secondary coil that powers the pump in the implant connected to the gastric band within the abdomen. Although batteries may be used to power the device, these long-term devices benefit from use of TET, allowing an implanted device of reduced size and complexity. Moreover, these devices may remain unpowered between adjustments, which provides additional advantages. These implantable, bi-directional infusing devices that would benefit from enhanced TET powering and/or telemetry are disclosed in four co-pending and co-owned patent applications filed on May 28, 2004, the disclosure of which are hereby incorporated by reference in their entirety, entitled (1) "PIEZO ELECTRICALLY DRIVEN BELLOWS INFUSER FOR HYDRAULICALLY CONTROLLING AN ADJUSTABLE GASTRIC BAND" to William L. Hassler, Jr., Ser. No. 10/857,762; (2) "METAL BELLOWS POSITION FEED BACK FOR HYDRAULIC CONTROL OF AN ADJUSTABLE GASTRIC BAND" to William L. Hassler, Jr., Daniel F. Dlugos, Jr., Rocco Crivelli, Ser. No. 10/856,971; (3) "THERMODYNAMICALLY DRIVEN REVERSIBLE INFUSER PUMP FOR USE AS A REMOTELY CONTROLLED GASTRIC BAND" to William L. Hassler, Jr., Daniel F. Dlugos, Jr., Ser. No. 10/857,315; and (4) "BI-DIRECTIONAL INFUSER PUMP WITH VOLUME BRAKING FOR HYDRAULICALLY CONTROLLING AN ADJUSTABLE GASTRIC BAND" to William L. Hassler, Jr., Daniel F. Dlugos, Jr., Ser. No. 10/857,763.

Unlike the previously mentioned medical implants, an infuser device for an artificial sphincter is typically implanted below a thicker dermal layer of skin and adipose tissue. This is particularly true for patients that typically receive an adjustable gastric band as a treatment for morbid obesity. Moreover, being more deeply implanted may allow for greater client comfort. However, the thickness of tissue presents difficulties for effective power coupling from a primary TET coil.

It is desirable that the secondary coil be encompassed within an outer case of the infuser device to enhance the integrity of the device. It is especially desirable to not have one or more secondary coils detached from the infuser device and implanted more superficially, as this complicates the implantation and explantation of the infuser device. Consequently, these generally known approaches to having spaced apart secondary coils to additively contribute to received signals are not appropriate. Further, there are physical and electromagnetic constraints to configuration of a secondary coil that is encompassed within a medical implant, especially the diameter, the number of turns of the coil, and the diameter of each turn.

Consequently, in order to provide for a larger power transfer range between the primary and secondary TET coils a significant need exists for enhancing power coupling with a deeply implanted medical device within the dimensional constraints imposed upon a secondary coil.

BRIEF SUMMARY OF THE INVENTION

The invention overcomes the above-noted and other deficiencies of the prior art by providing a transcutaneous energy transfer (TET) system for an implantable medical device that increases the number of turns on the secondary coil while maintaining the same impedance and Q factor (i.e., ratio of bandpass center frequency to 3 dB cutoff frequency) as a single coil configuration. Power transfer is increased to the secondary coil while relatively maintaining the same power on the primary coil.

In one aspect of the invention, a medical implant benefits from enhanced power transfer between an external primary TET coil and its secondary TET coil by splitting the secondary TET coil into two physically and electrically parallel coils. The effective number of magnetic flux collecting turns was doubled while maintaining the impedance, the inductance, capacitance, total tank circuit Q and natural frequency of the original secondary coil and tank circuit. By virtue thereof, a medical implant may be implanted more deeply for therapeutic reasons and for simplified implantation and explantation purposes, yet perform satisfactorily.

In another aspect of the invention, a TET system that includes both the implantable medical device and an external primary coil assembly achieve an enhanced power efficiency by the twin, electrically and physically parallel secondary TET coils.

In yet another aspect of the invention, an inductive energy transfer system for powering a device separated by a barrier from an external primary coil is enhanced by including a pair of electrically and physically parallel front and back secondary coils that are part of a resonant tank circuit.

These and other objects and advantages of the present invention shall be made apparent from the accompanying drawings and the description thereof.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 3A is a line graph comparing secondary power received at 20 kHz by the generally-known single secondary coil of FIG. 1 versus the twin secondary coil electrically connected in parallel of FIG. 2.

FIG. 3B is a line graph comparing primary power of the 310 turn 32-gauge coil to the two 325 turn 34-gauge coils connected in parallel at 20 kHz.

DETAILED DESCRIPTION OF THE INVENTION

Figure 1:
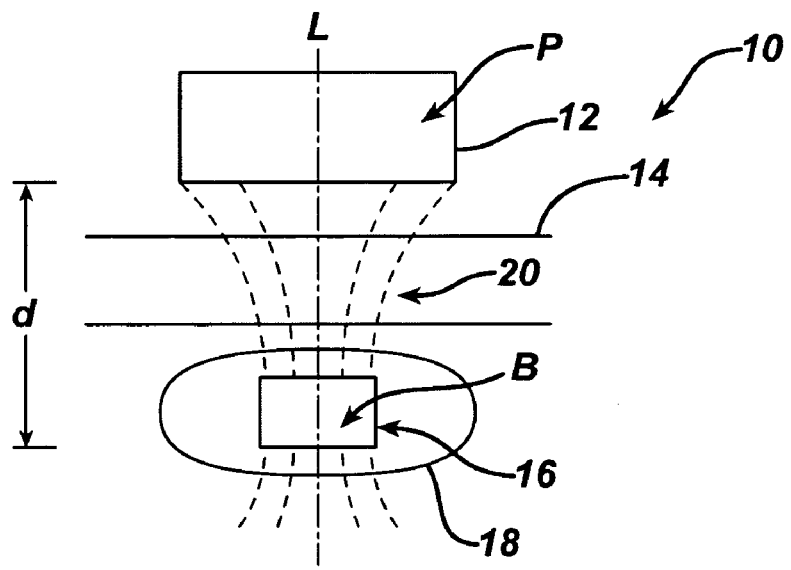
FIG. 1 is a diagram of a generally known primary coil aligned for transcutaneous power transfer and/or telemetry to a single secondary coil contained in an implanted medical device for powering electrical components therein.

In FIG. 1, a generally-known transcutaneous energy transfer (TET) system 10 provides power and/or telemetry between a primary coil 12, which is external to a dermal layer 14, to a secondary coil 16 within an implanted device 18, which is under the dermal layer 14. The primary coil 12 is inductively coupled to the secondary coil 16, as depicted by magnetic flux lines 20.

In developing a more efficient TET and/or telemetry system, and in particular the secondary coils of the system, it is necessary to optimize the combination of coil turns, DC resistance, tank circuit capacitance, tank circuit impedance and total tank circuit Q. Spatially optimizing a secondary coil design is largely dictated by how closely the secondary coil may be placed (distance "D") and longitudinally aligned (longitudinal axis "L") to the primary coil 12. Given constraints on the available volume and placement for the secondary coil 16 within implanted device 18, further maximization is generally available in this manner for a medical implant.

As an example of optimizing a single coil design, coils were wound with different wire gauges and turn ratios in order to create different impedances. These secondary coils 16 were made in a single coil configuration, the best configuration for a secondary coil 16. The best single coil configuration for the above mentioned infuser implant was 310 turns of 32-gauge magnet wire and was approximately 30 ohms DC resistance. The setup for the 310 turn 32 gauge secondary coil 16 is shown in FIG. 1. The highest power output that this coil provided to a fixed load under a set of test conditions was 3.96 Watts.

Figure 2:
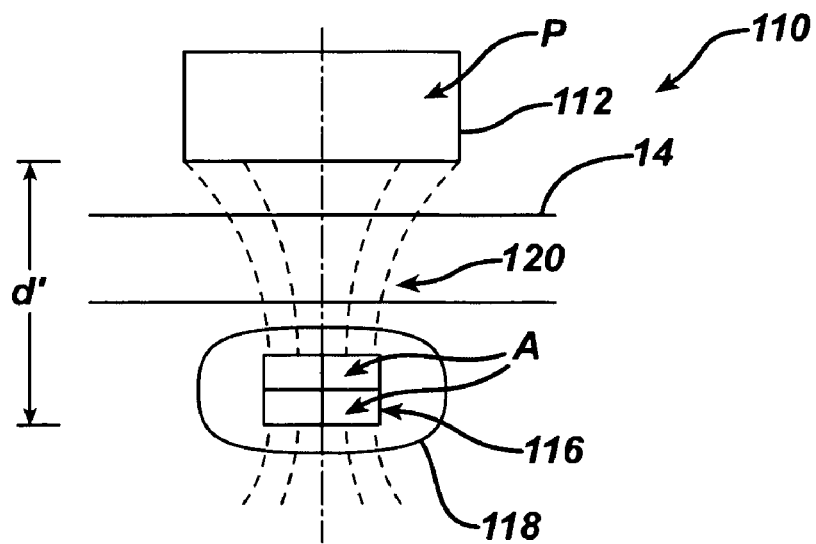
FIG. 2 is a diagram of a primary coil aligned for transcutaneous power transfer and/or telemetry to a twin secondary coil consistent with aspects of the present invention contained in an implanted medical device for enhanced powering electrical components therein.

In FIG. 2, a TET system 110 consistent with aspects of the invention provides power and/or telemetry between a primary coil 112, which is external to the dermal layer 14, to a double secondary coil 116, within an implanted device 118, which is under the dermal layer 14. Magnetic flux lines 120 denote increased power efficiency at a distance d' between coils 112, 116. A secondary coil was made-up of two coils in parallel, each having 325 turns of 34-gauge wire. This coil was approximately 30 ohms DC resistance and is shown in FIG. 2. The highest power that the two 325 turn 34 gauge coils in parallel provided to a fixed load under the same test conditions as the 310 turn 32-gauge coil was 4.46 Watts. A comparison of the power transfer curves of both coil arrangements is shown in FIGS. 3A and 3B. The power transfer curve for the two 325 turn 34-gauge coil arrangement has higher secondary power output than the single coil arrangement. However, the two 325 turn 34-gauge coil arrangement drew only a slight increase in primary power and is relatively the same size, impedance, and Q as the single coil arrangement, giving it a better efficiency.

Figure 4:
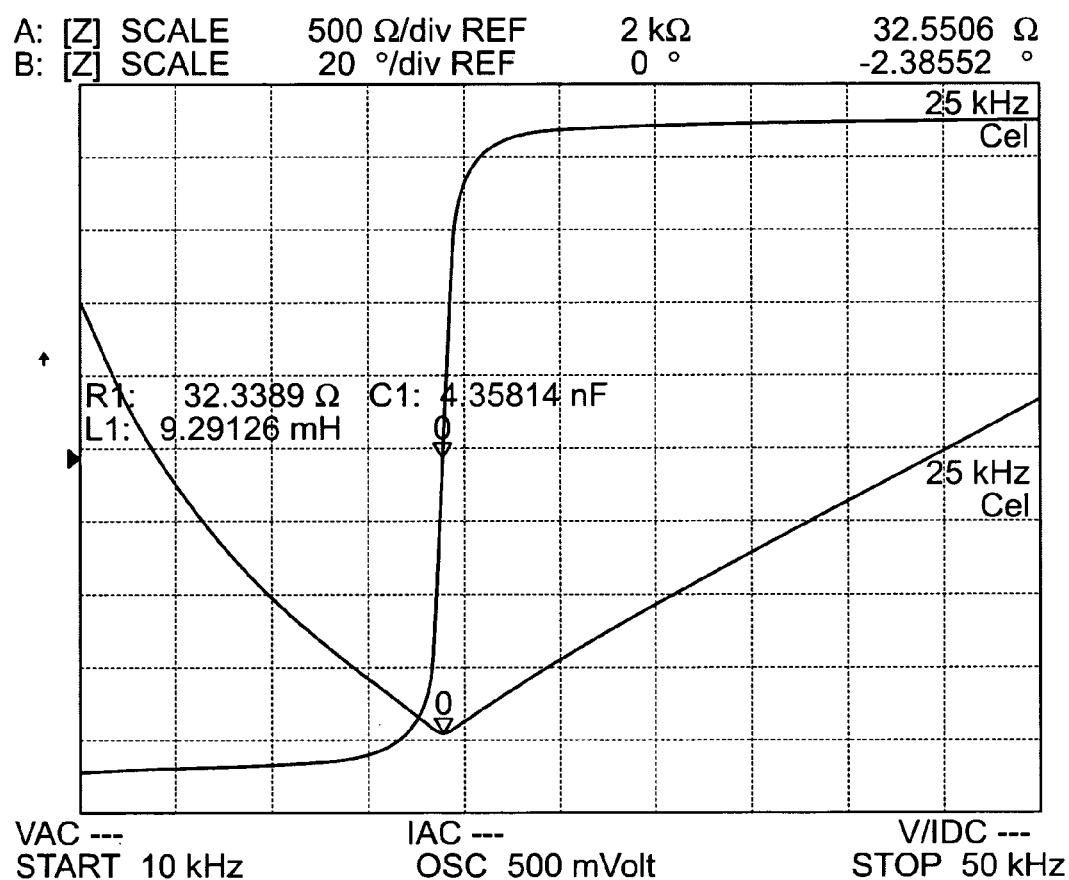
FIG. 4 is an impedance-phase plot of the twin secondary coil of FIG. 2.
Figure 5:
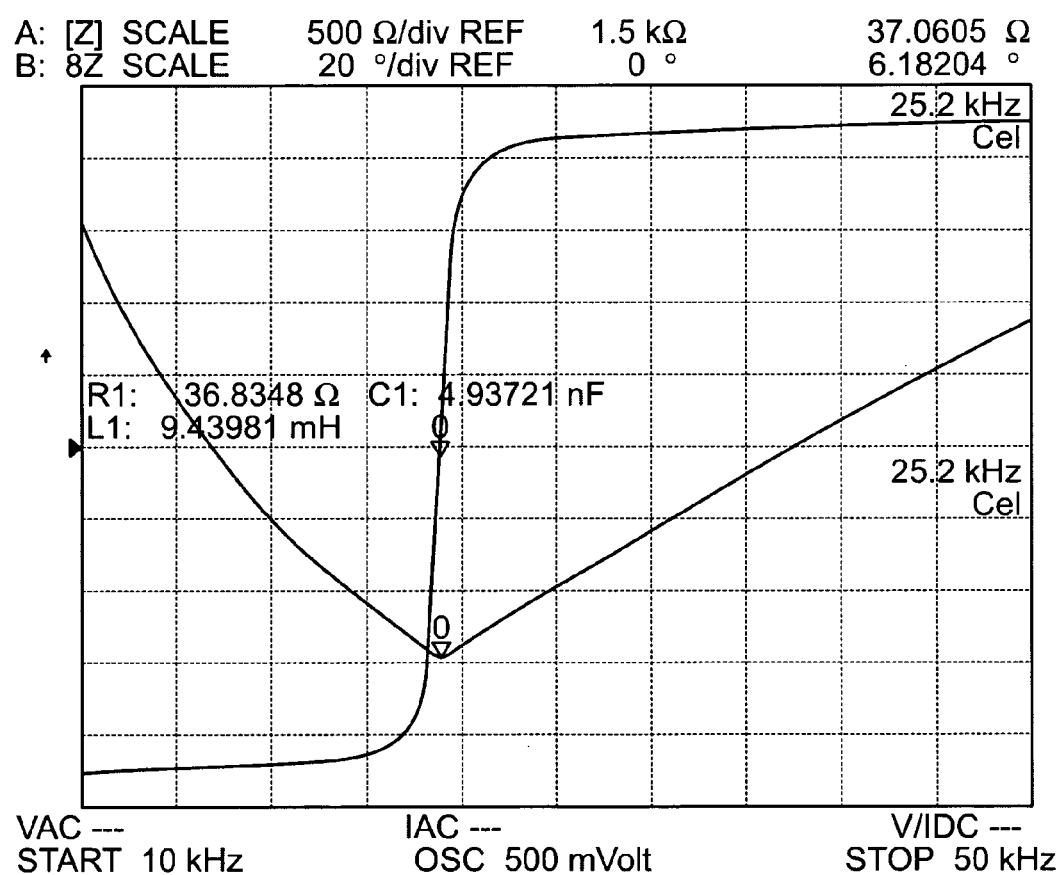
FIG. 5 is an impedance-phase plot of the generally known single secondary coil of FIG. 1.

The total impedances at resonance of both coils were relatively the same. In the illustrative version, a parallel combination of two impedances of 60 OHMS is equivalent to a single impedance of 30 OHMS. It proves theoretically how the 310 turn 32-gauge coil and the two 325 turn 34 gauge coil have the same total impedance. The impedance-phase plots of both coil arrangements were compared and found to be functionally equivalent as shown in FIGS. 4–5. Also, the total tank circuit Q value of the impedance plots of both coils were found to be relatively the same.

The two 325 turn 34-gauge coil arrangement gave a more optimum power transfer characteristic. It is not completely understood how this was accomplished, and it will probably require the use of electromagnetic finite element analysis (FEA) in order to fully understand this phenomenon. What is postulated is that by spatially spreading out the turns of the secondary coil as well as effectively doubling their number as far as coupling to the magnetic flux produced by the primary coil, the power transfer to the secondary was increased. This effect was not apparent by simple linear circuit analysis, which would conclude that the two coils were equivalent.

Figure 6:
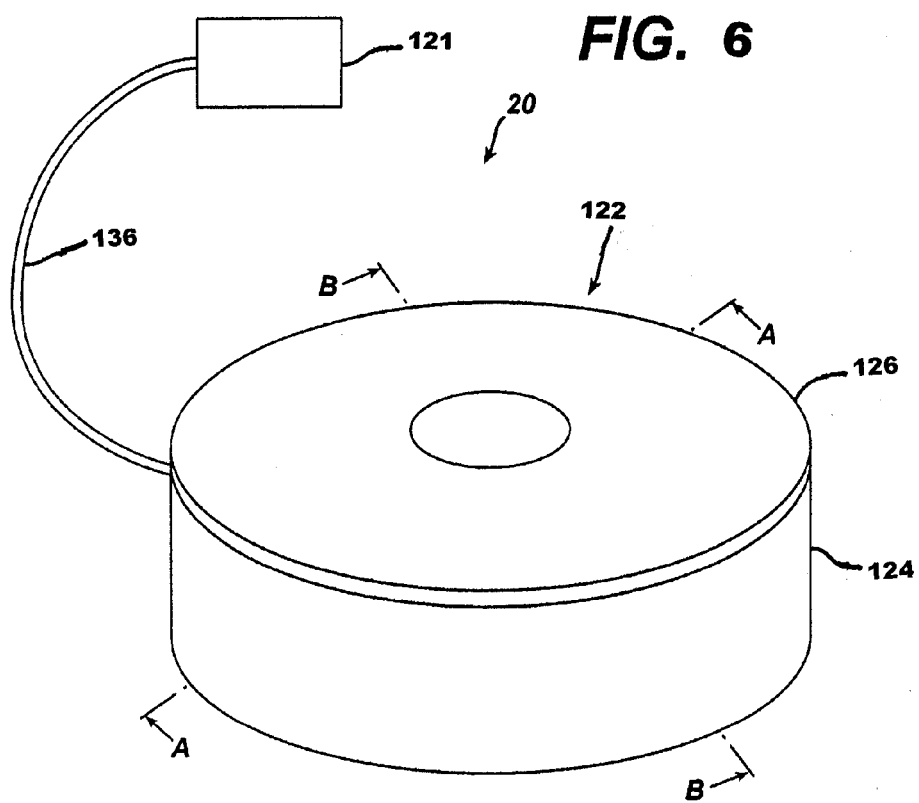
FIG. 6 is a diagrammatic view of a pump system in accordance with the present invention.

FIG. 6 provides a diagrammatic view of an implantable pump system 120 in accordance with one embodiment of the present invention. As will be described in more detail below, pump system 120 may be implanted under a patient's skin and controlled by an active telemetry system to direct fluid flow to and from a therapeutic implant. Although the invention is described herein with specific reference to the use of the implantable pump with an artificial sphincter 121, such as an adjustable gastric band, such description is exemplary in nature, and should not be construed in a limiting sense. The implantable pump of the present invention may also be utilized in any number of different apparatuses or systems in which it is desirable to provide bi-directional fluid flow between two interconnected subcutaneous components.

As shown in FIG. 6, the pump system 120 includes an implantable pump device 122 having a generally cylindrical outer casing 124 extending around the sides and bottom portions of the pump device 122, and an annular cover 26 extending across a top portion. Annular cover 126 may be of varying thickness, with the thickest portion located at the center 130 (shown in FIG. 7) of the cover 126. Casing 124 and cover 126 may be formed of titanium or another type of appropriate, non-magnetic material, as are the other parts of pump device 122 that are exposed to body tissue and fluids. The use of titanium or a similar material prevents pump device 122 from reacting to body fluids and tissues in which the pump device 122 may be implanted.

Figure 7:
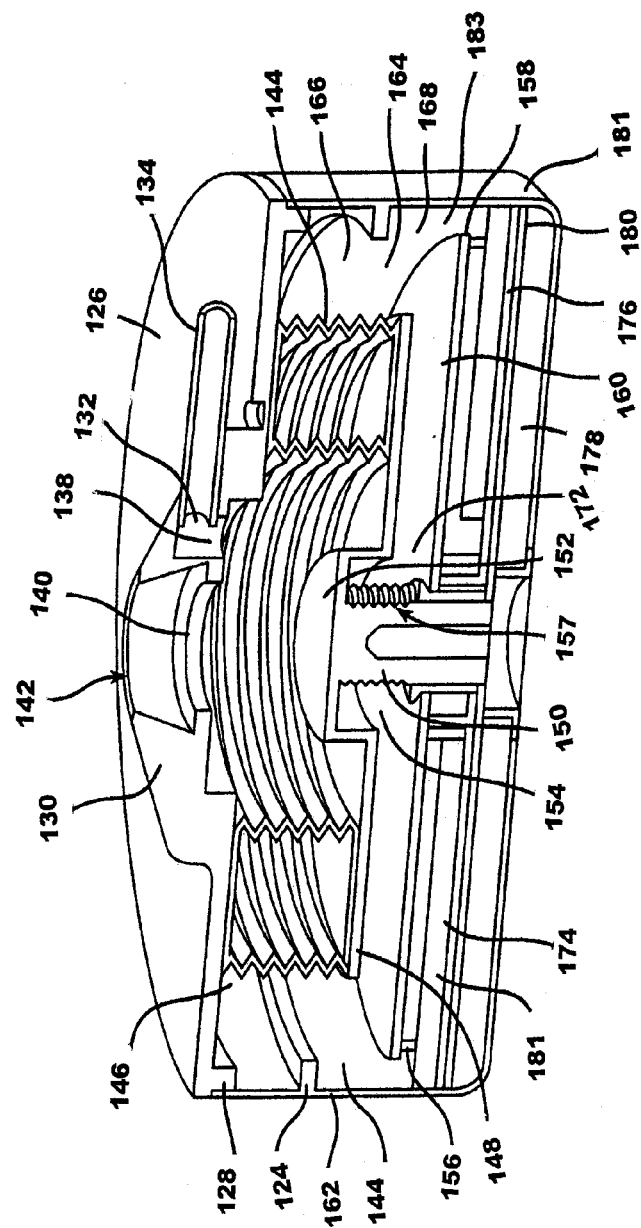
FIG. 7 is a cross-sectional view of an implantable pump of the pump system taken along line A—A of FIG. 6.
Figure 8:
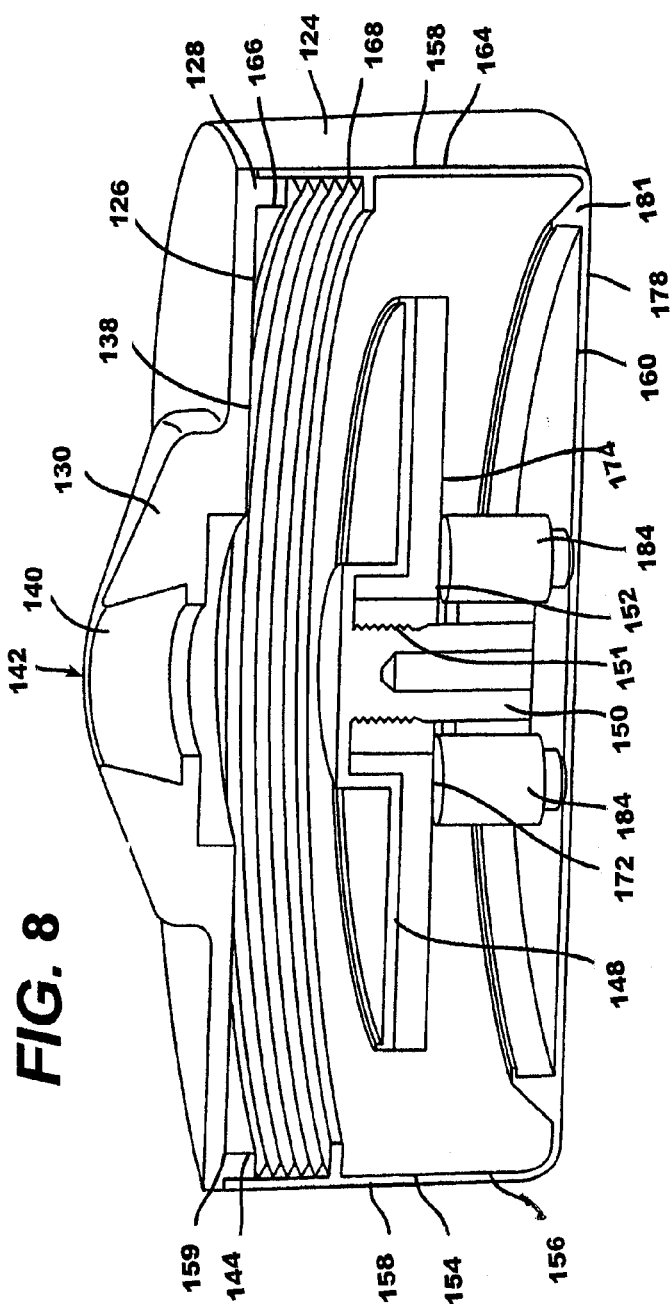
FIG. 8 is a cross-sectional view of the implantable pump taken along line B—B of FIG. 6.
Figure 9:
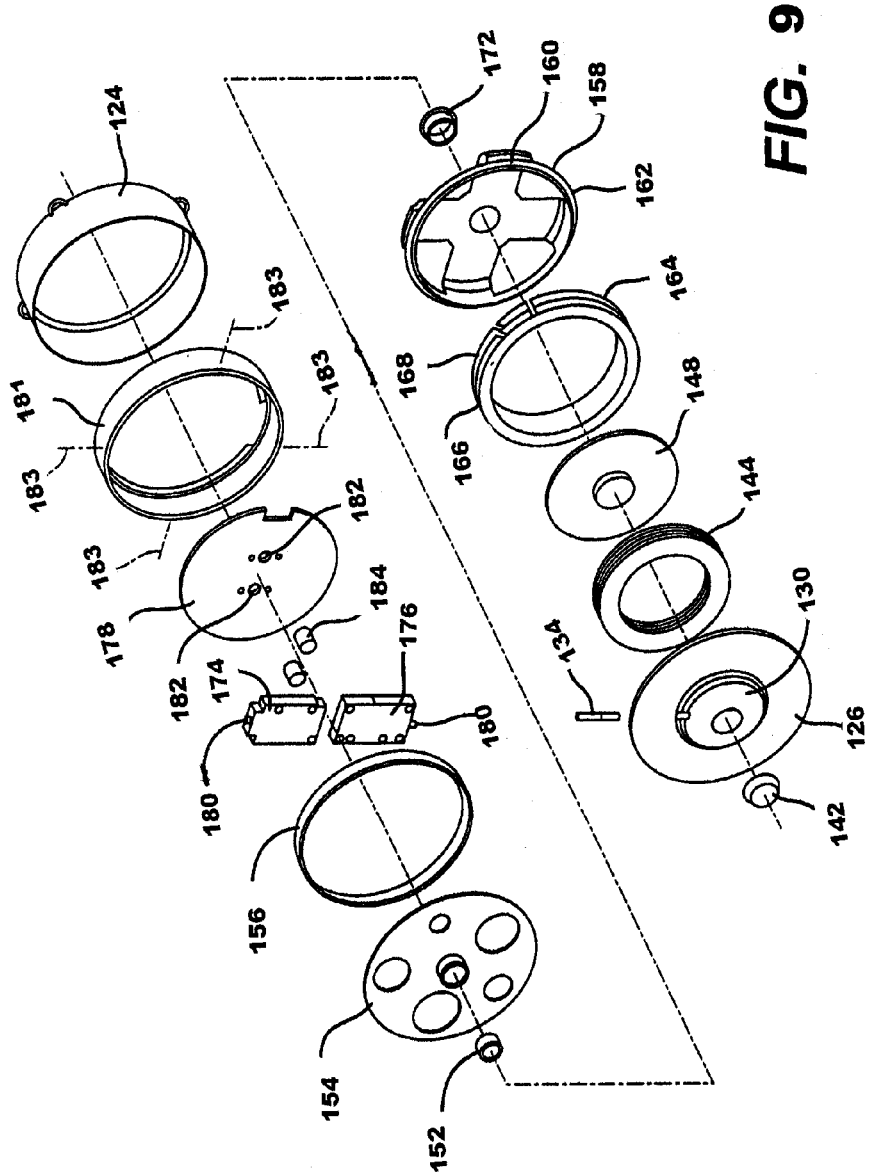
FIG. 9 is a front, exploded isometric view showing internal components of a first embodiment of the implantable pump of the present invention.
Figure 10:
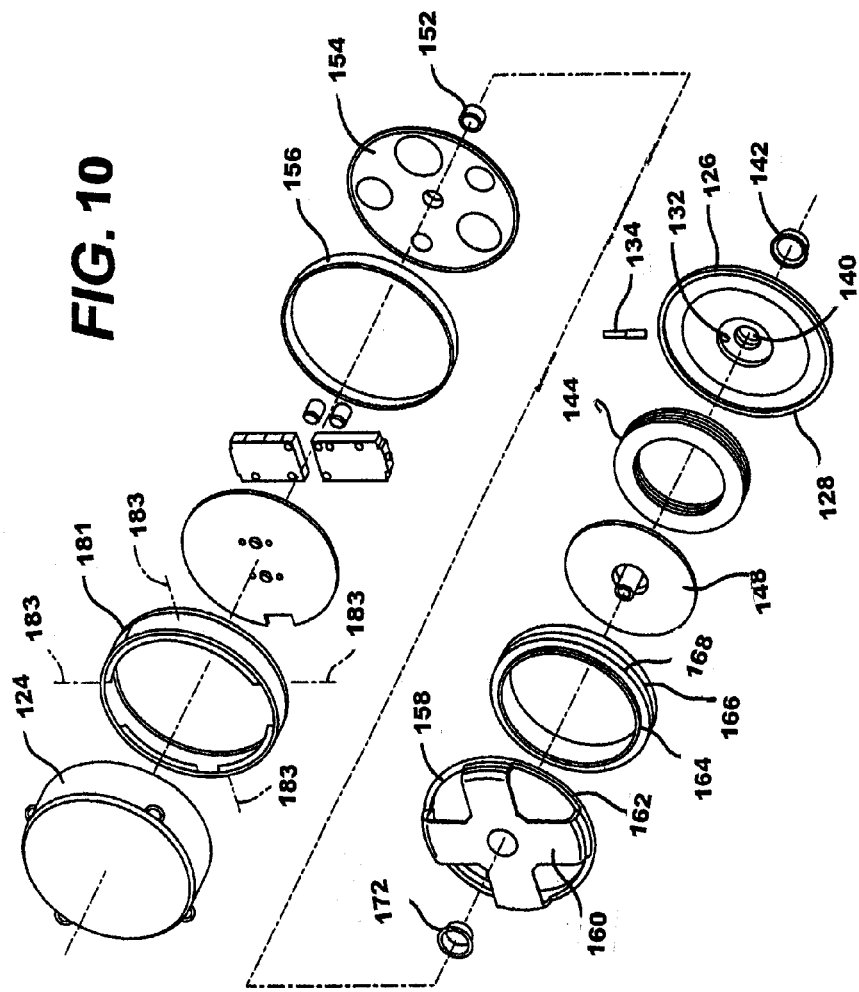
FIG. 10 is a rear, exploded isometric view showing internal components of the first embodiment of the implantable pump of FIG. 9.

FIGS. 7 and 8 are cross-sectional views showing the internal components of a first embodiment of pump device 122, with FIG. 8 being a 90° rotation of the FIG. 7 view. In addition, FIGS. 9 and 10 provide exploded isometric views from both the forward and rearward directions of pump device 122, illustrating the relative positions of the components within the pump device 122. As shown in FIGS. 7–10, thickened center portion 130 of cover 126 is molded or machined to include a duct 132. A catheter port 134 extends laterally from duct 132 in center portion 130 to connect with an external fluid-conveying device, such as, for example, a catheter 136 as shown in FIG. 6. Duct 132 connects catheter port 134 with a fluid reservoir 138 in the interior of pump device 122. Duct 132, catheter port 134 and catheter 136 combine to provide bi-directional fluid flow between fluid reservoir 138 and a secondary implant. As shown in FIGS. 6 and 7, cover 126 includes a port 140 into which a hypodermic needle (not shown) may be inserted either through the patient's skin, or prior to implantation of device 122, in order to increase or decrease the fluid volume in reservoir 138. A septum 142 is disposed in port 140 to enable infusions by a hypodermic needle while preventing other fluid transmissions through the port 140. Near the periphery of cover 126, an annular lip 128 extends downwardly in overlapping contact with casing 124. Casing 124 and cover 126 are welded together along lip 128 to form a hermetic seal.

Fluid reservoir 138 comprises a collapsible bellows 144 securely attached at a top peripheral edge 146 to cover 126. Bellows 144 are comprised of a suitable material, such as titanium, which is capable of repeated flexure at the folds of the bellows, but which is sufficiently rigid so as to be noncompliant to variations in pressure within reservoir 138. The lower peripheral edge of bellows 144 is secured to an annular bellows cap 148, which translates vertically within pump device 122. The combination of cover 126, bellows 144 and bellows cap 148 defines the volume of fluid reservoir 138. The volume in reservoir 138 may be expanded by moving bellows cap 148 in a downward direction opposite cover 126, thereby stretching the folds of bellows 144 and creating a vacuum to pull fluid into the reservoir. Similarly, the volume in reservoir 138 may be decreased by moving bellows cap 148 in an upward direction towards cover 126, thereby compressing the folds of bellows 144 and forcing fluid from the reservoir into duct 132 and out through catheter port 134.

As shown in FIGS. 7 and 8, bellows cap 148 includes an integrally formed lead screw portion 150 extending downwardly from the center of the cap 148. Lead screw portion 150 includes a screw thread, as indicated by numeral 151, that operatively engages a matching thread on a cylindrical nut 152. The mating threads 151 on lead screw portion 150 and cylindrical nut 152 enable the lead screw portion 150 to translate vertically relative to cylindrical nut 152 when the nut 152 is rotated about a longitudinal axis of the lead screw portion 150. The outer circumference of nut 152 is securely attached to an axial bore of a rotary drive plate 154. A cylindrical drive ring 156 is in turn mounted about an outer annular edge of rotary drive plate 154 to extend downwardly from the plate 154 on a side opposite to nut 152. Nut 152, drive plate 154 and drive ring 156 are all securely attached together by any suitable means, to form an assembly that rotates as a unit about the longitudinal axis formed by lead screw portion 150.

A bushing frame 158 is provided in pump device 122 and securely connected along a top edge to annular lip 128. Bushing frame 158 includes a bottom portion 160 extending beneath bellows cap 148, and a cylindrically-shaped side wall portion 162 spaced about the periphery of bellows 144. A cylindrical coil bobbin 164 extends about the inner circumference of frame 158, between the frame and bellows 144. One or more coil windings may be wound about the circumference of bobbin 164 for providing transcutaneous signal transfer between an external power and communication source and pump device 122. In the embodiment shown in FIGS. 7–10, a first coil winding 166 on bobbin 164 forms a closed loop antenna ("secondary TET coil") that is inductively coupled to a primary transcutaneous energy transfer (TET) coil in the external interface. When the primary TET coil in the external interface is energized, an RF power signal is transmitted to the secondary TET coil 166 to provide a power supply for driving pump device 122. A second coil winding 168 on bobbin 64 provides for control signal transfer between pump device 122 and an external programmable control interface. Coil winding 168 forms an antenna ("secondary telemetry antenna") that is inductively coupled to a primary telemetry antenna in the external device for transmitting RF control signals between the external interface and pump 122 at a fixed frequency. A bushing 172 is press fit into bushing frame 158 to extend between frame 158 and drive plate 154. Bushing 172 includes an axial opening for nut 152 and lead screw 150. Bushing 172 separates bushing frame 158 and drive plate 154 to allow the drive plate and nut 152 to rotate relative to lead screw 150 without interference between the bushing frame 158 and drive plate 154. In addition, bushing 172 prevents nut 152 from moving radially or axially toward cover 126.

As mentioned above, cylindrical nut 152, drive plate 154 and drive ring 156 form an assembly that translates lead screw 150 of bellows cap 148 when ring 156 is rotatably driven. In the first embodiment of the present invention, drive ring 156 is rotatably driven by one or more piezoelectric harmonic motors that utilize a series of harmonic vibrations to generate rotation in the ring. In the embodiment shown in FIGS. 7–10, a pair of harmonic motors 174, 176 are placed in frictional contact with the inner circumference of drive ring 156, so that the harmonic motion of the motors in contact with the ring produces rotation of the ring 156. Motors 174, 176 may be spaced 1800 apart about the inner circumference of ring 156, beneath drive plate 154. Motors 174, 176 are mounted to a support board 178, with a tip portion 180 of each motor in frictional contact with the inner circumferential surface of drive ring 156. When motors 174, 176 are energized, tips 180 vibrate against drive ring 156, producing a "walking" motion along the inner circumference of the ring 156, thereby rotating the ring 156.

A spring (not shown) within each motor 174, 176 biases motor tip portions 180 into continuous frictional contact with ring 156 to enable precise positioning of drive ring 156, and a holding torque on the ring 156 between motor actuations to prevent position shift in the ring 156. Drive ring 156 may be manufactured from a ceramic, or other similar material, in order to provide for the required friction with motor tip portions 80 while also limiting wear on the tip portions 180.

It should be appreciated by those skilled in the art having the benefit of the present disclosure that a piezoelectric harmonic motor, or another type of harmonic motor having no intrinsic magnetic field or external magnetic field sensitivity may be used in the present invention to enable patients with the implant to safely undergo Magnetic Resonance Imaging (MRI) procedures, or other types of diagnostic procedures that rely on the use of a magnetic field. The use of a piezoelectric harmonic motor rather than an electromagnetic servomotor in the present invention enables the device to provide the same high resolution, dynamic performance of a servomotor, yet is MRI safe. An example of a suitable piezoelectric harmonic motor for the present invention is the STM Series Piezoelectric Motor produced by Nanomotion Ltd. of Yokneam, Israel. This motor is described in detail in "The STM Mechanical Assembly and the Nanomotion Product/Selection Guide", both published by Nanomotion, Ltd. Other types of harmonic motors may also be utilized in the present invention without departing from the scope of the invention. Examples of these other motors include, without limitation, the Elliptec motor by Elliptec AB of Dortmund Germany, which is described in the "Elliptec Resonant Actuator Technical Manual. Version 1.2"; the Miniswys motor by Creaholic of Switzerland; the PDM130 Motor by EDO Electro-Ceramic Products of Salt Lake City, Utah which is described in the technical brochure "High Speed Piezoelectric Micropositioning Motor Model PDA130"; and the Piezo LEGS motor which is manufactured by PiezoMotor Uppsala AB of Uppsala, Sweden and described in the brochure entitled "Linear Piezoelectric Motors by PiezoMotor Uppsala AB". Additionally, piezoelectric inchworm motors may be utilized to drive a ceramic ring or plate, which motion is then translated into movement of a bellows. Examples of suitable piezoelectric inchworm motors include the IW-800 series INCHWORM motors produced by Burleigh EXPO America of Richardson, Tex. and the TSE-820 motor produced by Burleigh Instruments, Inc of Victor, N.Y. In addition, other types of rotary friction motors, and other types of motors which rely upon piezoelectric effects to drive a member may also be used without departing from the scope of the invention.

As discussed above, each motor 74, 76 in the first embodiment is mounted to a board 78 using a plurality of screws or other type of secure attachment mechanism. While two motors are depicted in the figures, additional motors may be utilized provided the driving member of each motor is in frictional contact with the drive ring. In addition to supporting motors 74, 76, board 78 may also include control circuitry for powering and operating the motors in accordance with signals transmitted from an external device. Alternatively, a separate circuit board could be included in pump device 22 that would include the circuitry for controlling motors 74, 76. The control circuitry on board 78 is electrically connected to coil windings 66, 68 for receiving power to drive motors 74, 76, as well as receiving and transmitting control signals for pump 22. Board 78 is attached to a wire assembly sheath 81, which is in turn connected by pins 83 to bushing frame 58. The connection between board 78 and frame 58 forms a mechanical ground to prevent the board and attached motors 74, 76 from torquing within pump device 22 when the motors are energized. As shown in FIGS. 3–5, board 78 may also include one or more openings 82 for retaining plate supports 84. Supports 84 extend between motors 74, 76, from board 78 to drive plate 54, to support the drive plate 54 and constrain the plate 54 from moving axially away from bellows 44.

Figure 11:
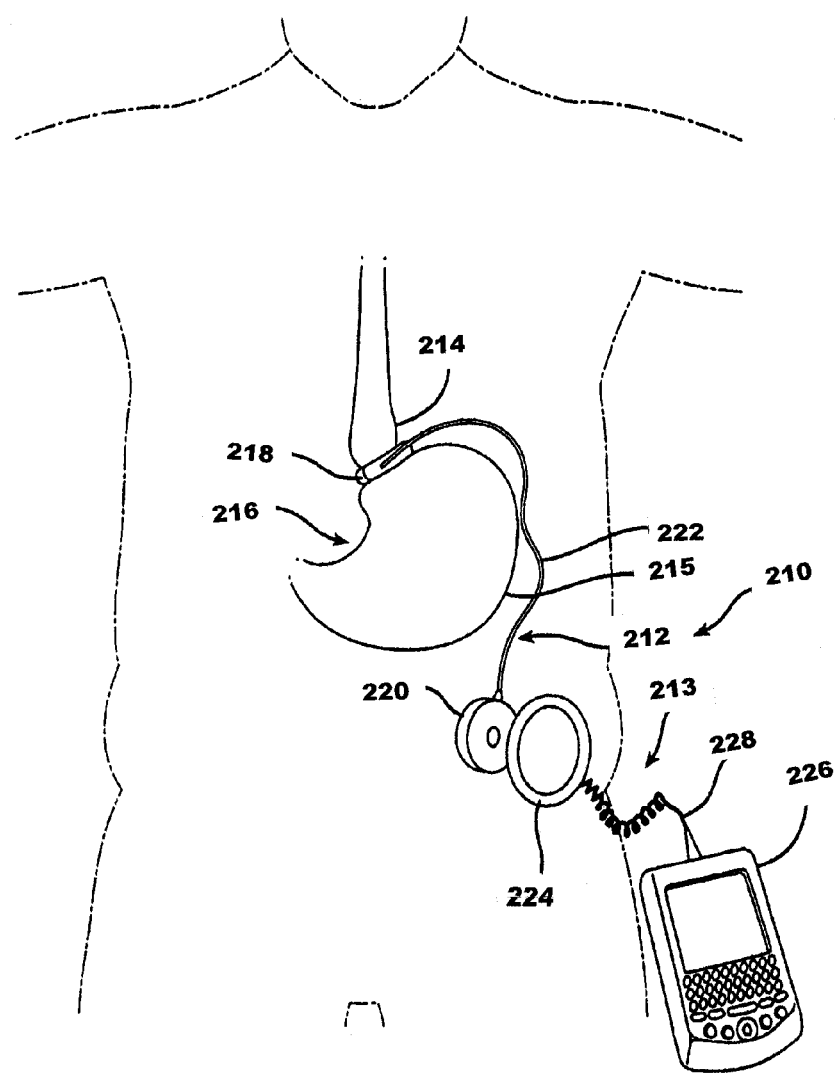
FIG. 11 is a perspective environmental view of an adjustable artificial sphincter system being closed-loop remotely controlled based upon volume sensing.

In FIG. 11, an artificial sphincter system 210 regulates the amount of fluid maintained in an implantable artificial sphincter assembly 212 powered by transcutaneous energy transfer (TET) and under telemetry control of an external assembly 213. In the illustrative version, the artificial sphincter system 210 is used for weight reduction therapy. A stoma is formed between an upper portion 214 and lower portion 215 of a patient's stomach 216 to slow the passage of food and to provide a sense of fullness. The implantable artificial sphincter assembly 212 includes an expandable gastric band 218 that encircles the stomach 216 to form the stoma. An infuser device 220 is anchored subcutaneously on a layer of muscular fascia within the patient or in another convenient location. A flexible catheter 222 provides fluid communication between the gastric band 218 and the infuser device 220.

It should be appreciated that the gastric band 218 includes an inwardly directed bladder to expandably receive a fluid, such as saline solution, from the catheter 222 to allow adjustment of the size of the stoma formed therein without having to adjust the attachment of the gastric band 218. The infuser device 220 advantageously prevents fluid moving in either direction between adjustments so that long-term implantation is realized.

An advantageous approach to reducing the necessary size of the infuser device 220 is to utilize TET for powering actuation and control circuitry from the external portion 213. Telemetry relays the amount of fluid in the infuser device 220 to the external assembly 213 for display, and in some applications for closing the loop on volume adjustment. To that end, the external system 213 may include a primary coil 224 positioned outside of the patient proximally placed to the infuser device 220 that is inside of the patient to inductively couple with a secondary coil (not shown) located within the infuser device 220. A programmer 226, which is connected via electrical cabling 228 to the primary coil 224, activates and monitors the primary coil 224.

Figure 12:
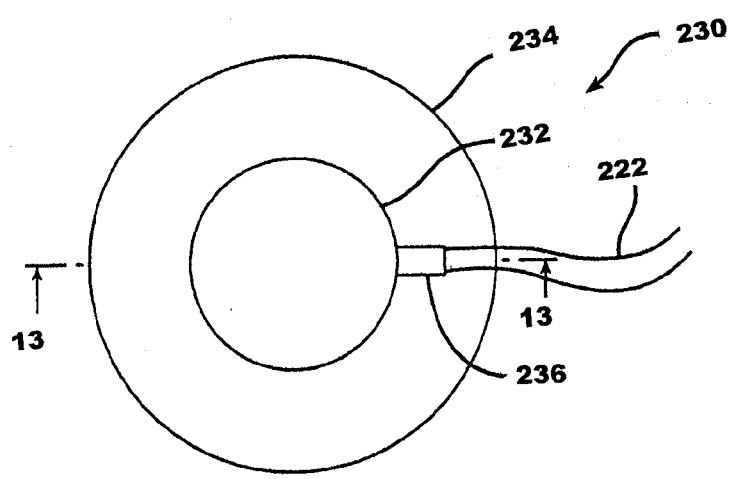
FIG. 12 is a top plan view of a bi-directional infuser device of the adjustable artificial sphincter system of FIG. 11.
Figure 13:
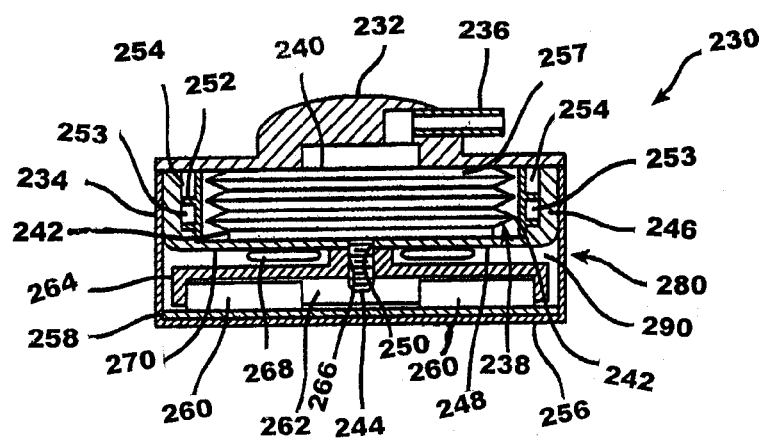
FIG. 13 is a sectioned side elevation view of the infuser device of FIG. 12, taken along section line 13—13, showing a version of a bellows accumulator position sensor based on variable inductance, and showing a bellows in an extended position.
Figure 14:
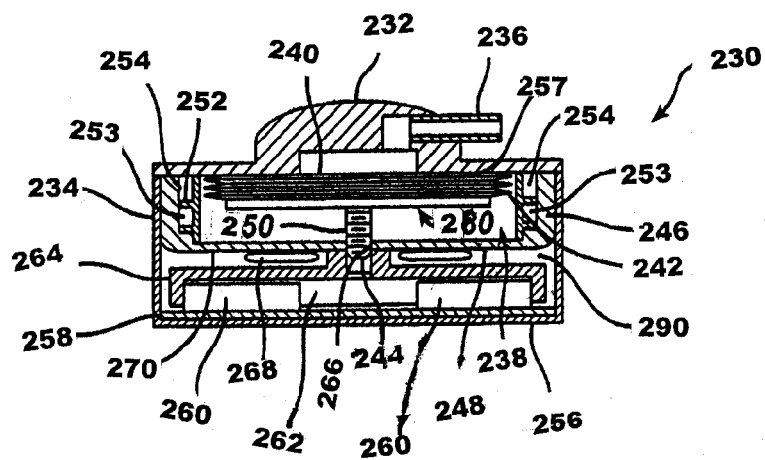
FIG. 14 is a sectioned side elevation view of the infuser device of FIG. 12, similar to FIG. 12, but showing a bellows in a collapsed position.

With reference to FIGS. 12–14, an implantable infuser device 230 incorporates inductive volume sensing. Infuser device 230 includes a fluid discharge head 232 and a cylindrical outer casing 234 sealed hermetically thereto, such as by welding. Discharge head 232 has a discharge conduit 236 sealably attached thereto and in fluid communication with a cylindrical bellows fluid accumulator ("bellows") 238. Bellows 238 has an open (fixed) end 240 welded to an inner surface of discharge head 232. Bellows 238 also has a closed (moving) end 242 fixedly attached to a lead screw 244 centered at the longitudinal axis of bellows 238 and extending away from bellows 238. Lead screw 244 has fine male threads such as ¼"–32 thereon.

Connected to and extending from discharge head 232 surrounding the circumference of bellows 238 is a cylindrical member 246 having a rigid bottom surface 248 and a clearance hole 250 centered therein through which lead screw 244 passes. Press-fit inside cylindrical member 246 and outside the perimeter of bellows 238 is a cylindrical bobbin 252 for housing spaced-apart secondary telemetry and transcutaneous energy transfer wire coils (not shown) in annular coil cavities 253, 254 formed with the cylindrical member 246, for receiving an actuation signal and induced power respectively from outside the patients body to operate the infuser device 230.

Cylindrical outer casing 234 has a base 256 substantially parallel to the inner surface 257 of discharge head 232. Fixedly attached to this base 256 is control circuitry, depicted as a circuit board 258, which contains a microprocessor and other electronic devices for operating the infuser device 230. Attached to circuit board 258 are two piezoelectric motors 260 symmetrically spaced about lead screw 244, having drive mechanisms frictionally contacting an inner rim 262 of a disk 264 centered about lead screw 244. Disk 264 has an internally threaded boss 266 extending therefrom toward bellows 238. Threaded boss 266 has matching ¼"–32 threads, which accurately mate with threads of lead screw 244 to form a nut which when rotated with disk 264 by motors 260 about lead screw 244, drive lead screw 244 and bellows 238 axially to expand or collapse the bellows 238. Motors 260 and TET/telemetry coils (not shown) are electrically connected to circuit board 258, all contained within outer casing 234.

It is desirable to sense the extended or collapsed position of bellows 238 to closed-loop control that position in order to accurately transfer a desired volume of fluid to and from the bellows 238. To that end, a pancake inductance coil 268 is placed in fixed position parallel to and axially aligned with closed end 242 of bellows 238. Coil 268 is preferably attached to a rigid bottom surface 270 of cylindrical member 246, for example, to minimize the distance between the coil 268 and the closed end 242 of the bellows 238. A parallel tuned tank circuit on circuit board 258, commonly known in the electronic controls art, oscillates at a frequency of resonance depending on the number and diameter of turns in inductance coil 268, the electrical capacitance in parallel with coil 268, and the closeness of closed end 242 to coil 268, forming an inductive position sensor 280. In the illustrative version, inductance coil 268 is a spiral shaped coil of about 200 turns made of 40 gauge copper wire. A microprocessor on the circuit board 258 measures the frequency of oscillation and compares it to a table of frequencies in order to provide an error signal to indicate how close the actual bellows position is to the command position desired. Piezoelectric motors 260, combined with driven disk 264 and threaded boss 266, actuate the bellows 238 via lead screw 244, forming a bellows actuators 290.

It should be appreciated that a position sensor that is not dependent upon the presence and/or rotation of a lead screw such as the afore-described inductive position sensor may have application in an infuser device that is thermodynamically actuated, such as described in the afore-mentioned cross-referenced applications.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein, will only be incorporated to the extent that no conflict arises between that incorporated material and the existing disclosure material.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

For example, while the TET system 16 described has particular advantages for an implantable medical device system 10, aspects consistent with the present invention have application to other scientific and engineering scenarios including inanimate physical boundaries. For instance, in a processing apparatus it may be desirable to monitor and/or control an actuator that is contained within a vessel without compromising the integrity of the vessel with wires or conduits passing therethrough.

For another example, TET for the purposes of power transfer to operate implanted devices has been illustrated above, although applications consistent with aspects of the invention may be directed to TET for communication purposes (i.e., telemetry). Thus, the power coupling efficiencies enhance the reliability and performance of the resultant communication channel.

For a further example, additional power transfer efficiencies may be realized by adding additional coils in physical and electrical parallel to the two described above with circuit optimization to maintain an appropriate Q and impedance, and thus a secondary twin coil is not limited to only two coils.

What is claimed is:

1. An implantable medical device that communicates with a primary transcutaneous energy transfer (TET) circuit external to a patient via a transcutaneous energy transfer channel, the implantable medical device comprising:
    a housing
    a first TET coil received by the housing;
    a second TET coil received by the housing, electrically coupled in parallel with the first TET coil, and physically proximate to and centered on a longitudinal axis of the first TET coil; and
    control circuitry in electronic communication with the parallel first and second TET coils and operably configured to utilize power transferred to the first and second TET coils.

2. The implantable medical device of claim 1, wherein the housing includes a coil receptacle comprising a cylindrically recessed portion of the housing.

3. The implantable medical device of claim 1, wherein the housing includes a coil receptacle comprising a cylindrical bobbin.

4. The implantable medical device of claim 1, wherein the first and second TET coils each are comprised of a coil formed having about 325 turns.

5. The implantable medical device of claim 4, wherein the first and second TET coils comprise 34 gauge magnetic wire.

6. The implantable medical device of claim 1, wherein the control circuitry comprises a telemetry transceiver.

7. The implantable medical device of claim 1, further comprising a series capacitance in electrical communication with the first and second TET coils to form a resonant tank circuit having a center frequency of about 20 kHz.

8. The implantable medical device of claim 1, further comprising a third TET coil electrically coupled in parallel with the first and second TET coils, and physically proximate to and centered on the longitudinal axis of the first and second TET coils, wherein the control circuitry in electronic communication with the parallel first, second and third TET coils is further operably configured to utilize power transferred to the first, second and third TET coils.

9. A transcutaneous energy transfer (TET) system, comprising:
    a primary transcutaneous energy transfer (TET) circuit external to a patient; and
    an implantable medical device, comprising:
        a housing including a coil receptacle having a longitudinally aligned and proximate first portion and second portion,
        a first TET coil received by the first portion of the coil receptacle,
        a second TET coil received by the second portion of the coil receptacle electrically coupled in parallel with the first TET coil,
        resonance circuitry in electrical communication with the first and second TET coils to form a resonant tank circuit, and
        control circuitry in electronic communication with the parallel first and second TET coils and operably configured to utilize power transferred to the first and second TET coils.

10. The transcutaneous energy transfer (TET) system of claim 9, wherein the coil receptacle comprises a cylindrically recessed portion of the housing.

11. The transcutaneous energy transfer (TET) system of claim 9, wherein the coil receptacle comprises a cylindrical bobbin.

12. The transcutaneous energy transfer (TET) system of claim 9, wherein the first and second TET coils each are comprised of a coil formed having about 325 turns.

13. The transcutaneous energy transfer (TET) system of claim 12, wherein the first and second TET coils comprise 34-gauge magnetic wire.

14. The transcutaneous energy transfer (TET) system of claim 9, wherein the control circuitry comprises a telemetry transceiver.

15. The transcutaneous energy transfer (TET) system of claim 9, further comprising a series capacitance in electrical communication with the first and second TET coils to form a resonant tank circuit having a center frequency of about 20 kHz.

16. An inductive energy transfer system, comprising:
   a primary coil assembly operably configured to induce a magnetic field having a resonant frequency through a barrier; and
   a separate device spaced apart from the primary coil assembly by the barrier, the separate device comprising:
      a front secondary coil substantially longitudinally aligned to an axis of the primary coil,
      a back secondary coil electrically coupled in parallel with, physically proximate to, and aligned parallel with the front secondary coil,
      resonance circuitry in electrical communication with the front and back secondary coils to form a resonant tank circuit having a pass band selected to encompass the resonant frequency of the primary coil assembly, and
      control circuitry in electronic communication with the parallel front and back secondary coils and operably configured to utilize electrical power received therefrom.

17. The inductive energy transfer system of claim 16, further comprising a housing encompassing the separate device and including a coil receptacle having a longitudinally aligned and proximate first portion and second portion to receive respectively the front and back secondary coils.

18. The inductive energy transfer system of claim 17, wherein the coil receptacle comprises a cylindrically recessed portion of the housing.

19. The inductive energy transfer system of claim 17, wherein the coil receptacle comprises a cylindrical bobbin.

20. The inductive energy transfer system of claim 16, wherein the front and back secondary coils each are comprised of a coil formed having about 325 turns.

21. The inductive energy transfer system of claim 20, wherein the front and back secondary coils comprise 34-gauge magnetic wire.

22. The inductive energy transfer system of claim 16, wherein the control circuitry comprises a telemetry transceiver.

23. The inductive energy transfer system of claim 16, further comprising a series capacitance in electrical communication with the first and second TET coils to form a resonant tank circuit having a center frequency of about 20 kHz.

* * * * *